United States Patent
Schonholz et al.

(10) Patent No.: US 10,034,785 B1
(45) Date of Patent: Jul. 31, 2018

(54) SINGLE SITE ACCESS AORTIC ANEURYSM REPAIR METHOD

(71) Applicant: W.L. Gore and Associates Inc., Newark, DE (US)

(72) Inventors: Claudio J Schonholz, Charleston, SC (US); Joshua D Adams, Mount Pleasant, SC (US)

(73) Assignee: W. L. Gore & Associates, Inc., Newark, DE (US)

( * ) Notice: Subject to any disclaimer, the term of this patent is extended or adjusted under 35 U.S.C. 154(b) by 106 days.

(21) Appl. No.: 15/292,003

(22) Filed: Oct. 12, 2016

Related U.S. Application Data

(60) Provisional application No. 62/240,554, filed on Oct. 13, 2015.

(51) Int. Cl.
| | |
|---|---|
| *A61F 2/82* | (2013.01) |
| *A61F 2/852* | (2013.01) |
| *A61F 2/958* | (2013.01) |
| *A61F 2/07* | (2013.01) |
| *A61F 2/966* | (2013.01) |
| *A61F 2/06* | (2013.01) |

(52) U.S. Cl.
CPC ............... *A61F 2/852* (2013.01); *A61F 2/07* (2013.01); *A61F 2/958* (2013.01); *A61F 2/966* (2013.01); *A61F 2002/067* (2013.01); *A61F 2002/826* (2013.01); *A61F 2210/0014* (2013.01)

(58) Field of Classification Search
CPC ....................................................... A61F 2/82
See application file for complete search history.

(56) References Cited

U.S. PATENT DOCUMENTS

| | | |
|---|---|---|
| 6,428,565 B1 | 8/2002 | Wisselink |
| 6,648,913 B1 | 11/2003 | Yee et al. |
| 6,773,454 B2 | 8/2004 | Toursarkissian et al. |
| 6,827,726 B2 | 12/2004 | Parodi |
| 6,918,925 B2 | 7/2005 | Tehrani |
| 6,918,926 B2 | 7/2005 | Letort |
| 6,942,692 B2 | 9/2005 | Landau et al. |
| 6,960,217 B2 | 11/2005 | Bulduc et al. |
| 7,229,472 B2 | 6/2007 | Depalma et al. |
| 7,267,685 B2 | 9/2007 | Butaric et al. |
| 7,438,721 B2 | 10/2008 | Doig et al. |
| 7,491,231 B2 | 2/2009 | Kujawski et al. |
| 7,637,932 B2 | 12/2009 | Bulduc et al. |
| 7,780,720 B2 | 8/2010 | Cragg et al. |
| 7,828,838 B2 | 11/2010 | Bulduc |
| 8,075,570 B2 | 12/2011 | Bolduc et al. |
| 8,083,792 B2 | 12/2011 | Rush et al. |
| 8,092,519 B2 | 1/2012 | Bolduc |
| 8,172,895 B2 | 5/2012 | Anderson et al. |

(Continued)

*Primary Examiner* — Matthew Schall

(57) ABSTRACT

A single access method of repairing an aneurysm in a bifurcated vascular lumen is described. A primary graft portion is configured in the bifurcated vascular lumen before a guide wire is configured through the primary graft portion and into a contralateral vessel of the bifurcated vascular lumen from the access opening. The guide wire may be a directed into the contralateral vessel and around the bifurcation in the primary graft portion by steerable sheath, a directional sleeve or a sheath having an aperture and secured to the primary graft portion by a balloon. The contralateral limb is then advanced through the access opening in the ipsilateral vessel, around the bifurcation and into the contralateral vessel.

23 Claims, 16 Drawing Sheets

(56) References Cited

U.S. PATENT DOCUMENTS

| | | |
|---|---|---|
| 8,192,482 B2 | 6/2012 | Cragg et al. |
| 8,475,513 B2 | 7/2013 | Sithian |
| 8,603,153 B2 | 12/2013 | Haverkost et al. |
| 8,632,579 B2 | 1/2014 | Banks et al. |
| 8,715,336 B2 | 5/2014 | Chu et al. |
| 8,945,202 B2 | 2/2015 | Welk et al. |
| 9,101,501 B2 | 8/2015 | Elicker et al. |
| 2003/0130725 A1 | 7/2003 | Depalma et al. |
| 2004/0117003 A1 | 6/2004 | Ouriel et al. |
| 2009/0299462 A1 | 12/2009 | Fawzi et al. |

SINGLE SITE ACCESS AORTIC ANEURYSM REPAIR METHOD

CROSS REFERENCE TO RELATED APPLICATIONS

This application claims the benefit of U.S. provisional patent application No. 62/240,554, filed on Oct. 13, 2015; the entirety of which is hereby incorporated by reference.

BACKGROUND OF THE INVENTION

Field of the Invention

This invention is directed to methods of repairing an aneurysm in a bifurcated vascular lumen through a single access in one of the branches of the bifurcated vascular lumen and is particular directed to aortic aneurysm repair

Background

In 1990 in Argentina Dr. Parodi and his team performed the first Endovascular Aortic Aneurysm Repair (EVAR) implanting a stent graft to treat Abdominal Aortic Aneurysm (AAA) using a 27 FR sheath through a cutdown of the femoral artery. Since then technology has improved in multiple aspects including reduction of size of the delivery systems and the use of percutaneous techniques that include closure devices. Despite these improvements, access continues to be a limiting factor in the treatment of patients using endovascular techniques and the site of potential complications including femoral artery dissection and occlusion and retroperitoneal or infrainguinal hematomas. Lower profile and even ultra-low profile devices will increase the success rate in patients with bad access and decrease overall access complications

SUMMARY OF THE INVENTION

The invention is directed to a bifurcated vascular lumen aneurysm repair method that enables repair through a single access opening. In an exemplary embodiment, the access opening is within one of the limbs of the bifurcated vascular lumen, wherein a bifurcated graft is assembled within the bifurcated vascular lumen through the single access opening. In an exemplary embodiment, the bifurcated vascular lumen comprises an aorta and the repair may be for an abdominal aortic aneurysm.

An exemplary method comprises initial placement of a primary graft portion comprising a main body within the bifurcated vascular lumen through an access opening in one of the limbs of the bifurcated vascular vessel. The distal end of the main body is secured within the vascular lumen distal the bifurcation of the vascular lumen. An ipsilateral limb may be integrally coupled with the main body and extend down into the ipsilateral vessel of the bifurcated vascular lumen. In an alternative embodiment, a main body comprises an ipsilateral branch and an ipsilateral limb is coupled to the ipsilateral branch and extends down into the ipsilateral vessel. In an exemplary embodiment, a contralateral branch extends from the main body and a contralateral limb is coupled to the contralateral branch through the same access opening in the ipsilateral vascular limb. A primary graft portion may be configured in the bifurcated vascular lumen through any conventional means and deployed or secured in position through any suitable means. An exemplary primary graft portion and limb coupled thereto may be a self-expanding stent graft comprising a deployment sleeve, may comprise a sheath that is removed to deploy the device, or may be a balloon expandable stent graft After placement of the primary graft portion, a contralateral limb is coupled to the primary graft portion. The proximal end of the contralateral limb is configured to extend from the contralateral branch into the contralateral vessel. The proximal end of the contralateral limb overlaps with the contralateral branch upon deployment, thereby coupling the contralateral limb to the primary graft portion. As described herein, the contralateral limb is introduced through an access opening in the ipsilateral vessel and traversed up the ipsilateral vessel, around the bifurcation in the vessel and into the contralateral vessel. A contralateral limb may be passed along a guide wire that was previously configured around the bifurcation and into the contralateral vessel.

In one embodiment, a steerable sheath is used to guide a guide wire around a bifurcated vessel. A guide wire may be introduced through the ipsilateral access opening and traversed up into the primary graft portion. A steerable sheath may then be passed over the guidewire with the distal end extending past the bifurcation. The distal end of the guide wire may then be pulled back within the sheath and the distal and steerable end of the sheath may then be directed in the direction of the contralateral vessel. The amount of the deflection of the steerable end of the steerable sheath may be controlled by an operator control, such as a knob or dial. The guide wire may then be traversed through the deflected steerable sheath down into the contralateral vessel. A contralateral limb may then be passed along the guide wire through the steerable sheath and into the contralateral vessel. An exemplary steerable sheath is the Heli-FX-guide available from Aptus Endosystems Inc. Sunnyvale, Calif. There are many directional sheaths available in the market that were designed for Electrophysiology trans-septal ablation procedures (Mobicath from Biosense Webster, Agilis Steerable Introducer from St. Jude Medical or Destino from Oscor); guiding sheaths for renal, SMA/Celiac PTA and stenting (Morph Deflectable guide catheter from Biocardia). In addition, a robotic steerable sheath may also be used. A robotic steerable sheath can be controlled from a remote location wherein the operator is not exposed to radiation within the operating room.

In another embodiment, a sheath is secured in position within the main body of the primary graft portion by a balloon and an aperture in the sheath allows a guide wire to be passed therethrough and deflected by the balloon into a contralateral branch of the bifurcated vascular lumen. The balloon may be positioned in the distal end of the main body. A guide wire introduced through the access opening in the ipsilateral vessel may be guided though the aperture and then deflected toward the contralateral vessel.

In still another embodiment, a direction sleeve is attached to the primary graft portion and comprises a proximal opening to the access opening in the ipsilateral vessel and extends around the graft bifurcation and has a distal opening that is directed toward the contralateral vessel. After placement of the primary graft portion, a guide wire may be introduced through the access opening in the ipsilateral vessel and traversed into the proximal opening of the direction sleeve, which directs the distal end of the guide wire around the graft bifurcation and toward the contralateral vessel. The guide wire can then be traversed into the contralateral vessel. A contralateral limb may then be passed along the guide wire, through the direction sleeve and at least partially into the contralateral vessel. The sleeve may be made out of, or comprise any suitable material, including polytetrafluoroethylene (PTFE), polyether ether ketone (PEEK), titanium, and the like. The directional sleeve may remain in the primary graft portion or may be configured to be detached from the primary graft portion and removed after placement and securing of the contralateral limb. A tether may extend from the directional sleeve and out through an access opening. After the bifurcated stent is assembled, the directional sleeve may be detached from the graft by manipulation, such as pulling, of the tether and removed through the access opening.

In an exemplary embodiment, the contralateral limb is introduced through the single access opening in the ipsilateral vessel and traversed along a guide wire, around the graft bifurcation and at least partially into the contralateral vessel, wherein the distal end of the contralateral limb is configured within the contralateral vessel. In a preferred embodiment, the contralateral limb is secured in position with the proximal end being secured first within the contralateral branch of the primary graft portion before the remainder of the contralateral limb is secured, such as by deployment or balloon expansion. In this securing method of the contralateral limb, the contralateral limb graft is deployed or secured along a proximal portion of the guide wire before the portion that is configured over a more distal portion of the guide wire. Securing the proximal end of the contralateral limb within the contralateral branch, or to the primary graft portion, first may better ensure proper positioning with respect to the primary graft portion. A contralateral limb may be secured however with the distal end being secured or deployed prior to a more proximal end.

An exemplary graft, including the primary graft portion and any limbs that are coupled thereto, is a covered stent graft comprising a cover material that is substantially impermeable to liquid flow, such as a fluoropolymer including, but not limited to, polytetrafluoroethylene (PTFE), fluorinated ethylene propylene (FEP), fluoroelastomers, composites or layered materials and the like. A graft may be a stent graft or covered stent graft comprising a stent made of metal, such as Nitinol. In an exemplary embodiment, the graft is a self-expanding covered stent graft that is configured in a deployment sleeve, available from W.L. Gore and Associates, Newark, Del. A deployment sleeve is configured to constrain the graft in a constricted configuration to facilitate passage through the access opening, the vasculature and through any sleeves or sheaths for guiding the device into the proper location. A deployment sleeve may be configured to release from a first end to a second end by manipulation of a release line that extends out of the access opening. The graft may expand in dimension or deploy from a first end to the second end as the release line is manipulated. A deployment sleeve may be configured to remain in the body after the graft is deployed. In another embodiment, a graft, as described herein, is configured within a sheath that is pulled off. Again, the graft may expand in dimension or deploy from one end to the other as the sheath is removed. In still another embodiment, a graft is a balloon expandable graft requiring an external force to expand the graft from a constricted configuration into an expanded configuration.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
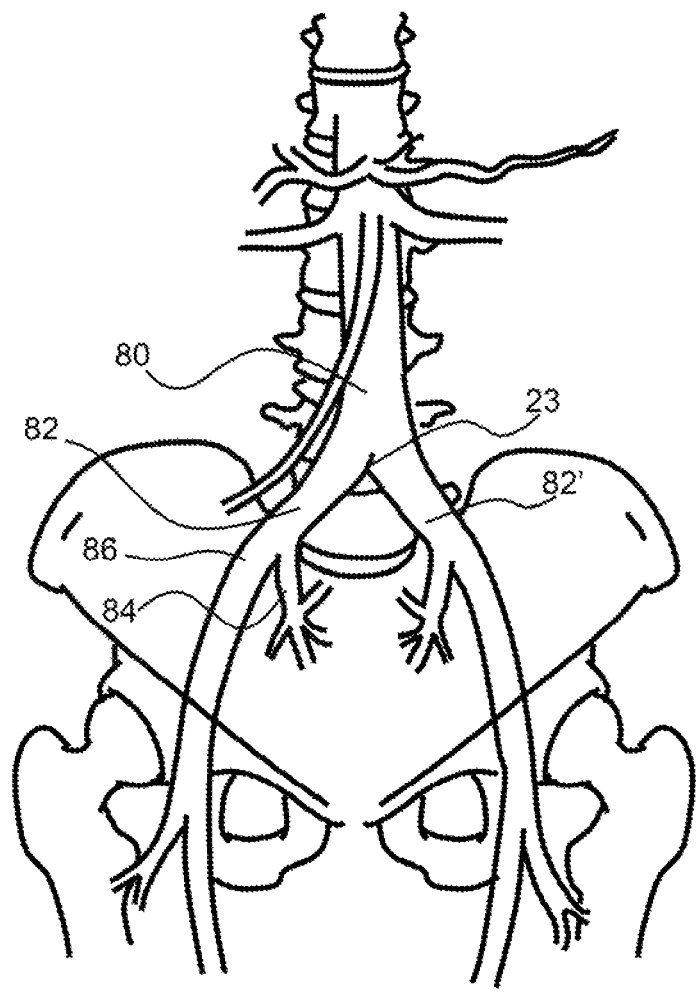
FIG. 1 shows a diagram of a portion of the vascular anatomy including the aorta and the iliac artery.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is clear that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

FIG. 1 shows a diagram of a portion of the vascular anatomy including the aorta 80 and the right and left iliac arteries 82, 82', respectively. This is a common area for aneurysm to form, either in the aorta prior to the bifurcation 23 and/or in the common iliac artery prior to the bifurcation into the internal 84, and external iliac 86 arties.

Figure 2:
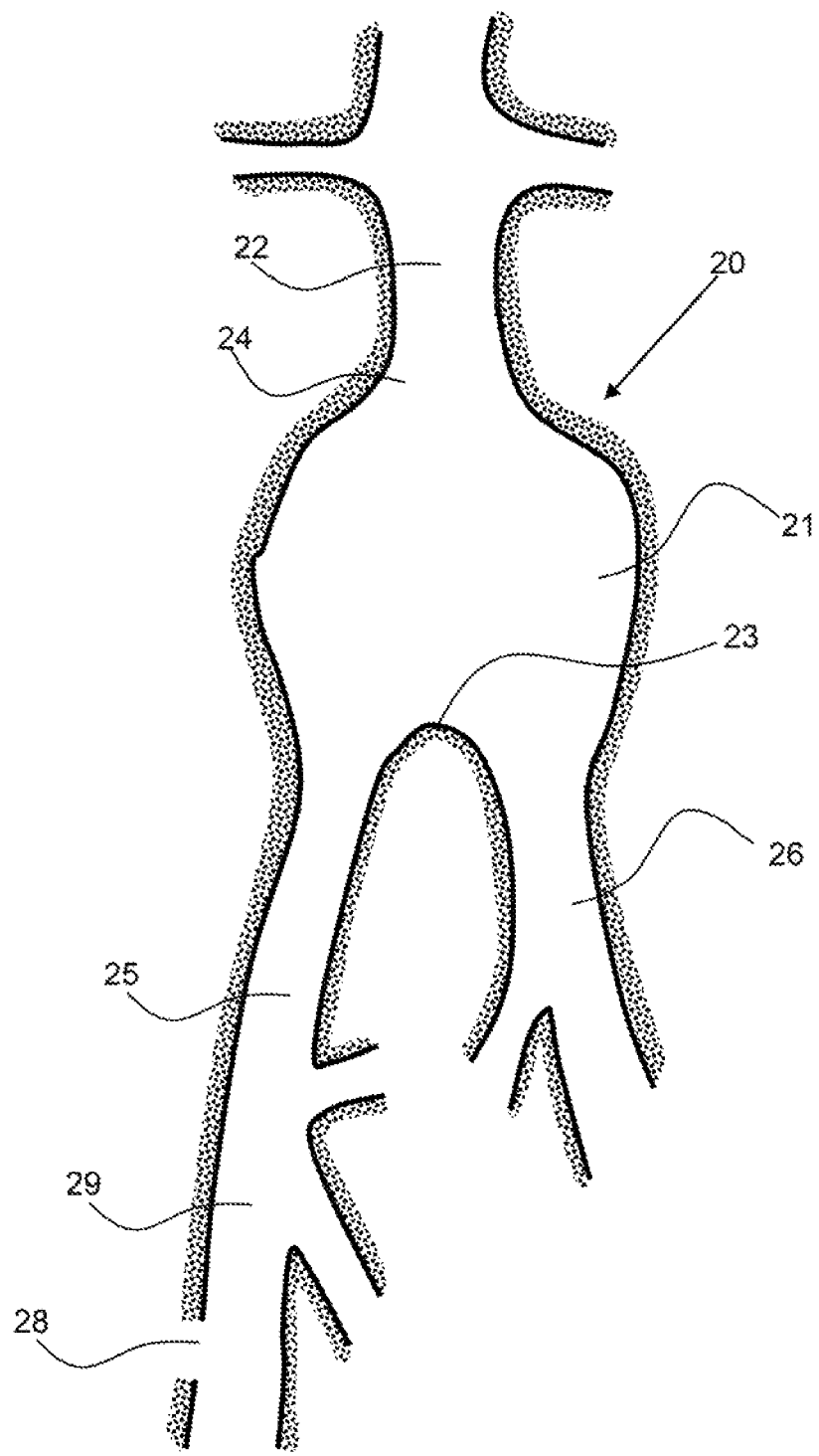
FIG. 2 shows a diagram of an exemplary bifurcated vascular lumen having an aneurysm.

As shown in FIG. 2, an exemplary bifurcated vascular lumen 20 has an aneurysm 21 just prior to the vessel bifurcation 23. The bifurcated vascular lumen 20 comprises a main vascular lumen 24 that branches into an ipsilateral vessel 25, or branch, and a contralateral vessel 26 or branch. An access opening 28 provides access to the interior conduit 29. A distal portion 22 of the main vascular lumen 24 is distal the aneurysm with respect to the access opening. The bifurcated vascular lumen shown is the aorta but could be any bifurcated vascular lumen.

Figure 3:
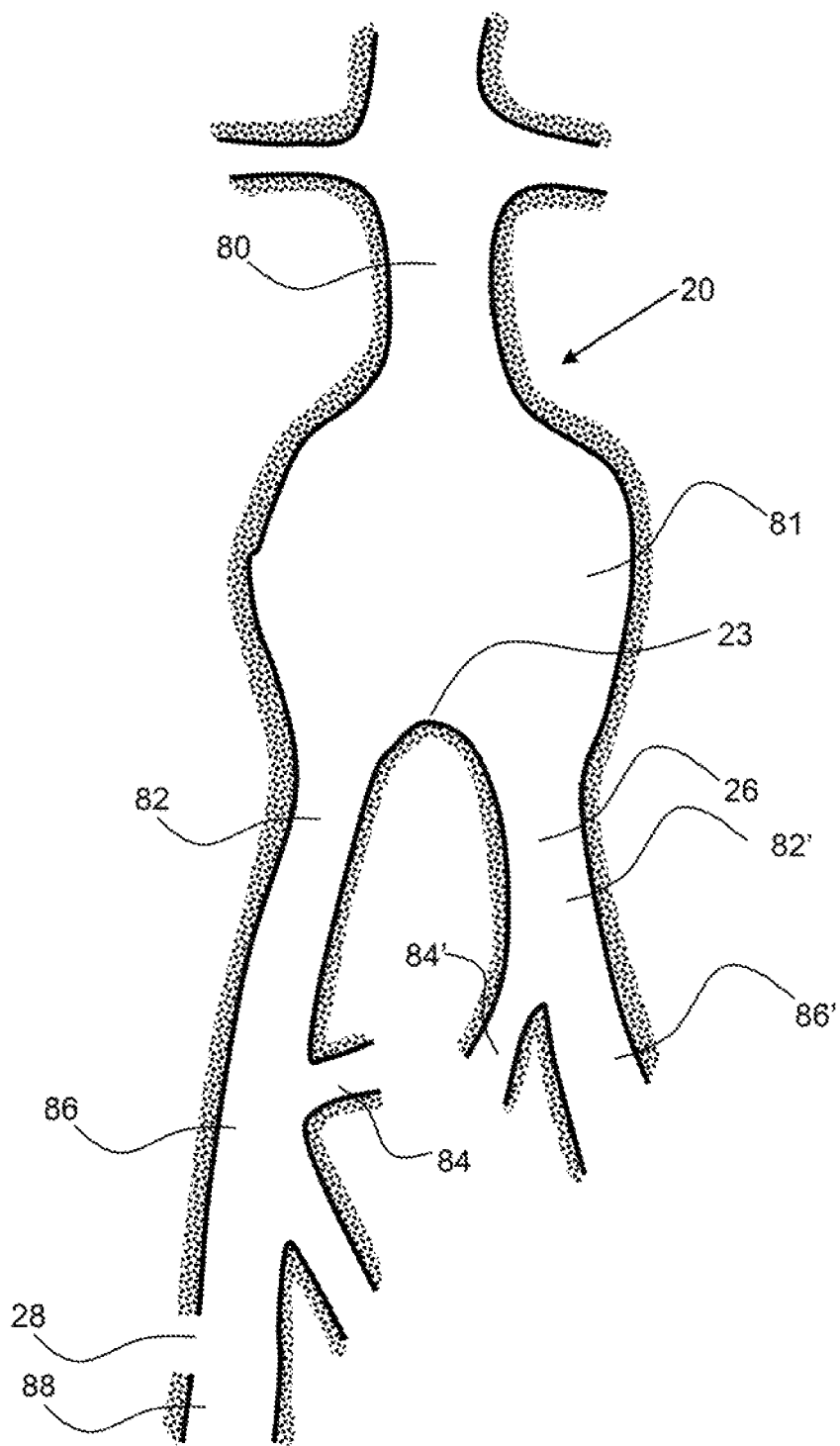
FIG. 3 shows a diagram of an abdominal aortic aneurysm.

FIG. 3 shows a diagram of an abdominal aortic aneurysm 81. The aorta 80 is distended just prior the bifurcation 23 into the right and left common iliac arteries 82, 82' respectively. An access opening 28 is configured in the femoral artery 88 and this access opening provides access to the right common iliac artery 82. The contralateral vessel or left common iliac artery 82' as well as both of the internal iliac arteries 84, 84' and external iliac arteries 86, 86' are shown.

Figure 4:
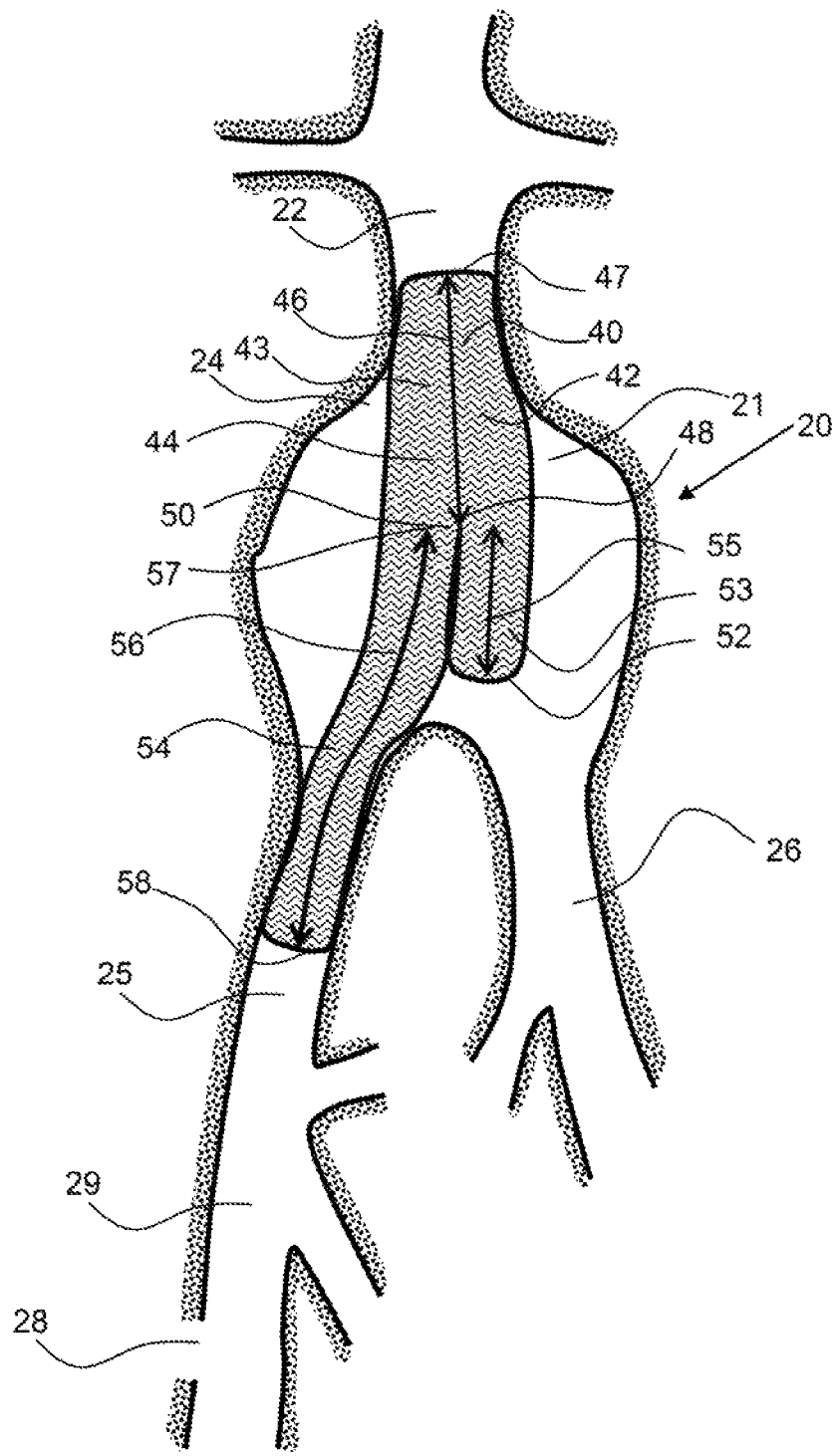
FIG. 4 shows an exemplary primary graft portion configured in the bifurcated vascular lumen with an integral ipsilateral limb extending down into the ipsilateral vessel.

As shown in FIG. 4, an exemplary primary graft portion 40 is configured in the bifurcated vascular lumen 20. The primary graft portion has a main body 43 that is a single tubular graft 42 having a length 46 from the distal end 47 to the flow divider 48, where the graft bifurcation 50 starts. The primary graft portion comprises an integral ipsilateral limb 54 having a length 56 from the graft bifurcation 50 to the extended end 58, proximal to the access opening 28. The primary graft portion has a contralateral branch 53 having a length 55 from the graft bifurcation 50 to the extended end 52 of the contralateral graft branch. It is to be understood that the primary graft portion 40 may comprise an opening, or a contralateral branch with a very short length for receiving the contralateral limb and may have substantially no contralateral branch. The distal end 47 of the main body 43 is secured in the distal lumen 22 and the integral ipsilateral limb is configured within the ipsilateral vessel 25 of the bifurcated vascular lumen 20. The primary graft portion 40 has a lumen that extends from the distal end of the main body 40 and down into the two separate lumens after the graft bifurcation 50.

Figure 5:
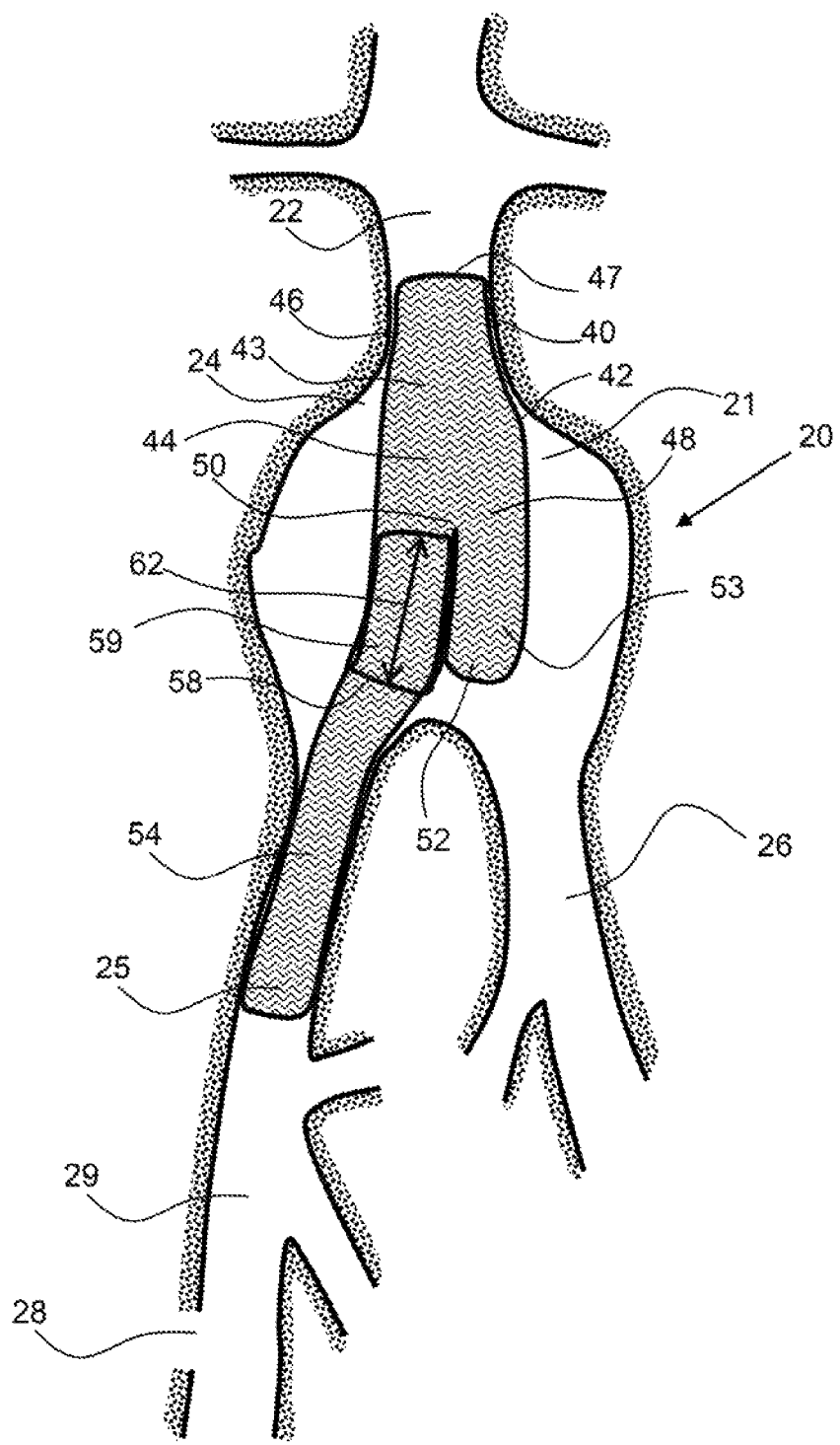
FIG. 5 shows an exemplary primary graft portion configured in the bifurcated vascular lumen with a separate ipsilateral limb coupled with an ipsilateral branch of the primary graft portion.

As shown in FIG. 5, an exemplary primary graft portion 40 is configured in the bifurcated vascular lumen 20. The primary graft portion has a main body 43. The primary graft portion comprises an integral ipsilateral branch 59 having a length 62 from the graft bifurcation to the extended end 58 of the ipsilateral branch. Note that the ipsilateral branch is slightly longer than the contralateral branch 53. An ipsilateral limb 54 is coupled to the primary graft portion 40, with an overlap within the ipsilateral branch 59. A bifurcated graft may comprise three components, a primary graft portion 40, and an ipsilateral limb and a contralateral limb that are coupled to the primary graft portion.

Figure 6:
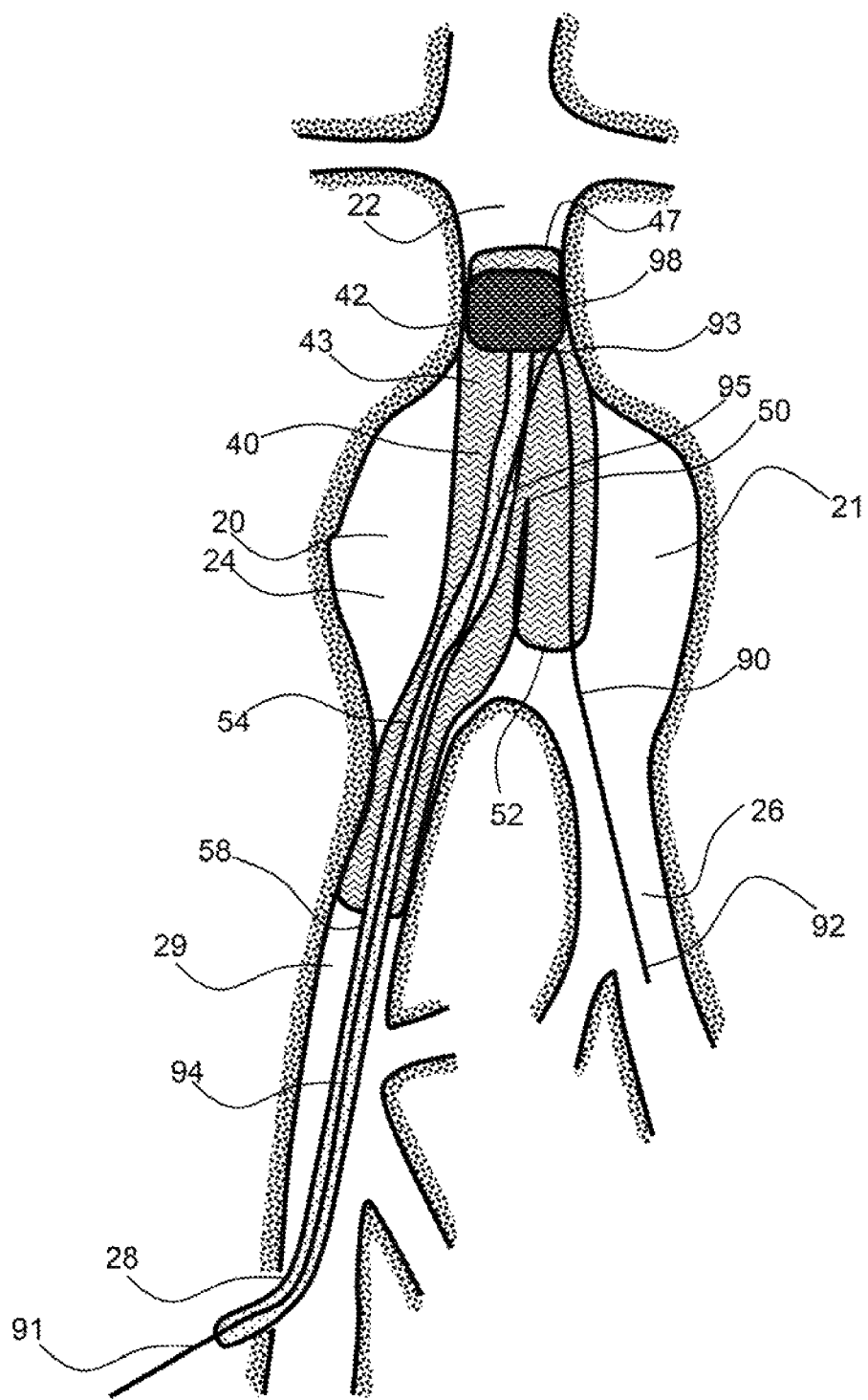
FIG. 6 shows an exemplary primary graft portion configured in the bifurcated vascular lumen, a sheath having a balloon expanded in the main body, and a guide wire extending through the sheath, out of an aperture in the sheath and into the contralateral vessel of the bifurcated vascular lumen.

As shown in FIG. 6, an exemplary primary graft portion 40 is configured in the bifurcated vascular lumen 20. A sheath 94 has a balloon 98 expanded in the main body 43 and a guide wire 90 extending through the sheath, out of an aperture 95 in the sheath, and into the contralateral vessel 26 of the bifurcated vascular lumen. The guide wire has a bend 93 where it is deflected towards the contralateral vessel by the balloon. The balloon acts as a deflector for the guide wire. The guide wire 90 has a proximal end 91 configured outside of the access opening 28 and a distal end 92 that is within the contralateral vessel 26.

Figure 7:
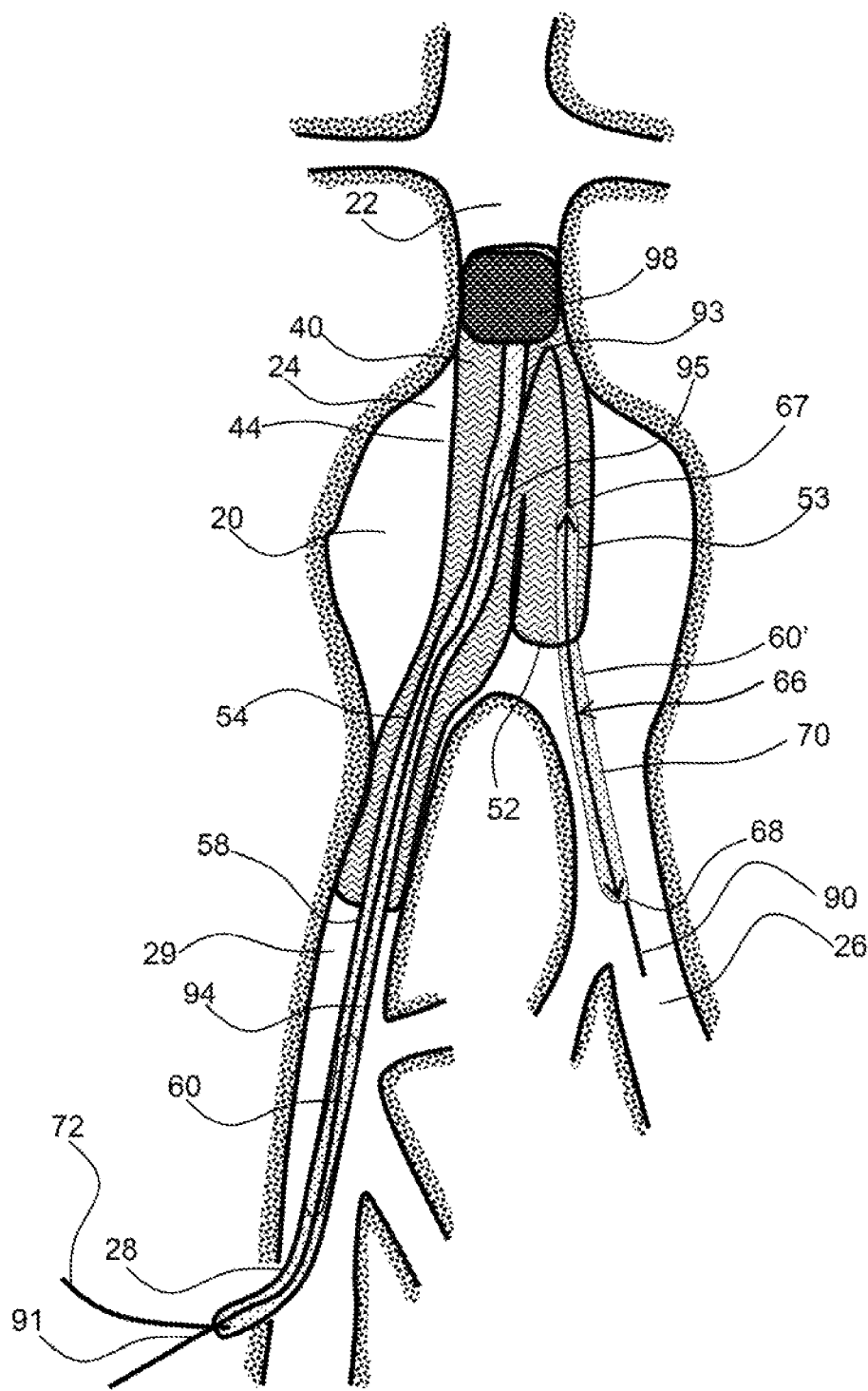
FIG. 7 shows a contralateral limb being passed along the guide wire through the aperture in the sheath and down into the contralateral vessel.

FIG. 7 shows a contralateral limb 60 being introduced through the access opening 28, through the sheath 94, along the guide wire 90, partially through the contralateral branch 53 and into the contralateral vessel 26. The contralateral limb 60' is within a deployment sleeve 70 that constricts the contralateral limb down in dimension, particularly in diameter. A release line 72 is coupled with the deployment sleeve and is configured to release the deployment sleeve from a first proximal end 67 to a distal end 68, or extended end from the primary graft portion 40. The contralateral limb, in this embodiment, is a self-expanding stent graft. The contralateral limb has a length 66 from a proximal end 67 to a distal end 68.

Figure 8:
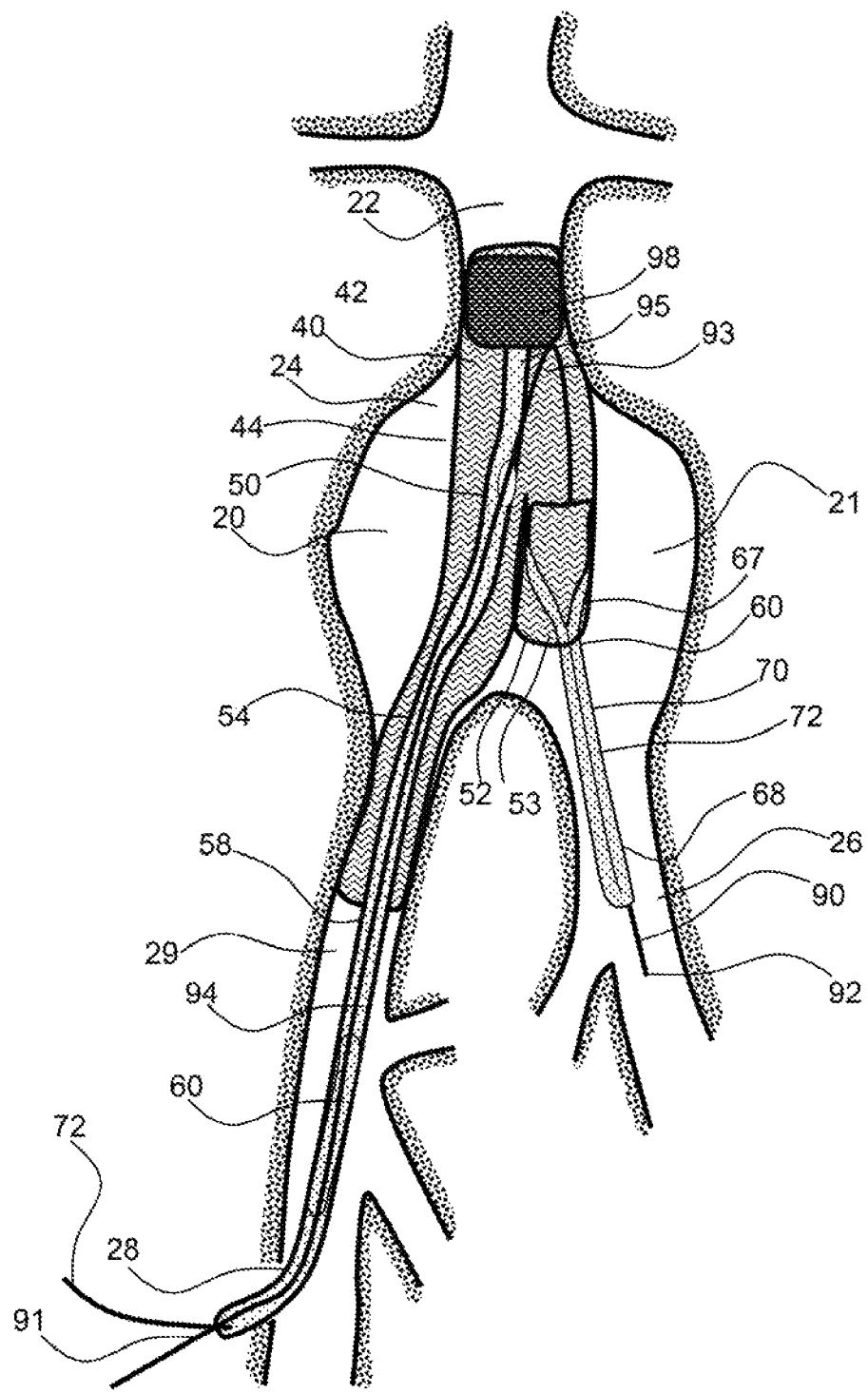
FIG. 8 shows the contralateral limb being deployed with the proximal end being expanded within the contralateral branch of the primary graft portion before the remainder of the contralateral limb.

FIG. 8 shows the contralateral limb 60 being deployed; wherein the proximal end 67 is being expanded or deployed before the remainder of the contralateral limb. The release line 72 is being pulled to unzip the deployment sleeve 70 from one end to the other. Expanding the proximal end of the contralateral limb first, secures the contralateral limb to the primary graft portion 40 before deployment of the rest of the contralateral limb.

Figure 9:
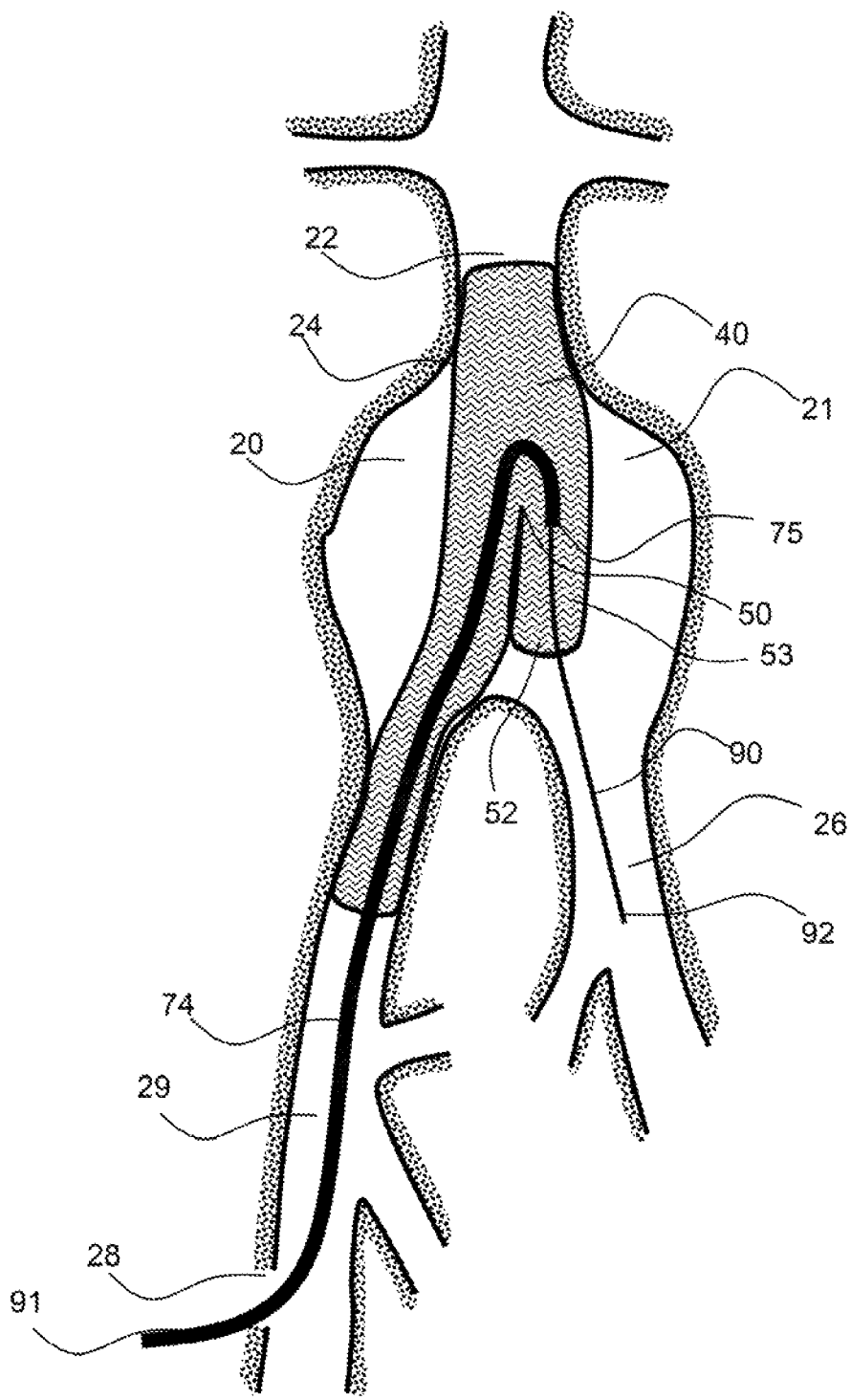
FIG. 9 shows an exemplary steerable sheath configured around the graft bifurcation.

FIG. 9 shows an exemplary steerable guide sheath 74 configured within the primary graft portion 40. The steerable end 75 of the steerable sheath is bent and can be directed through manipulation of controls by a user, such as a knob or dial. The guide wire 90 extends through the steerable sheath. In an exemplary method, the guide wire is introduced into the access opening 28 and traversed into the primary graft portion 40. The steerable sheath is then advanced over the guide wire and is deflected to point the distal, or steerable end 75, toward the contralateral vessel 26. The guide wire is then advanced through the sheath and into the contralateral vessel.

Figure 10:
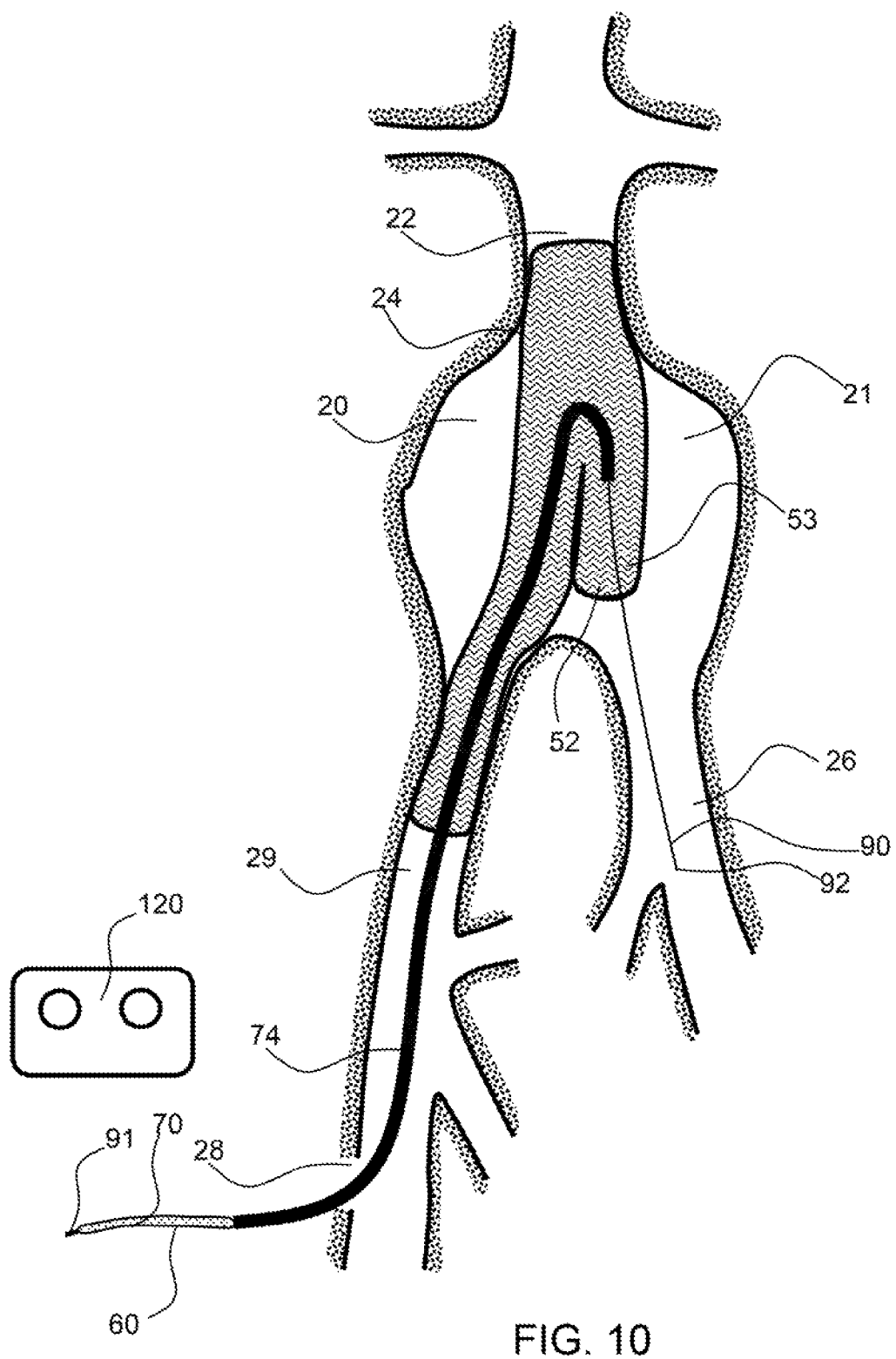
FIG. 10 shows a contralateral limb being introduced into the steerable sheath and along the guide wire therein.

FIG. 10 shows a contralateral limb 60 being passed through the access opening 28, through the steerable sheath 74 and along the guide wire 90. The contralateral limb 60 is configured within a deployment sleeve 70 that constricts the contralateral limb to a smaller dimension. The contralateral limb is a self-expanding stent graft in this embodiment. The distal end 92 of the guide wire has been positioned in the contralateral vessel 26. An operator controller 120 for the steerable sheath 74 is shown schematically that is operated by a clinician outside of the patient's body, in this embodiment having at least two dials for deflecting and directing the steerable sheath around the bifurcation and into the contralateral branch.

Figure 11:
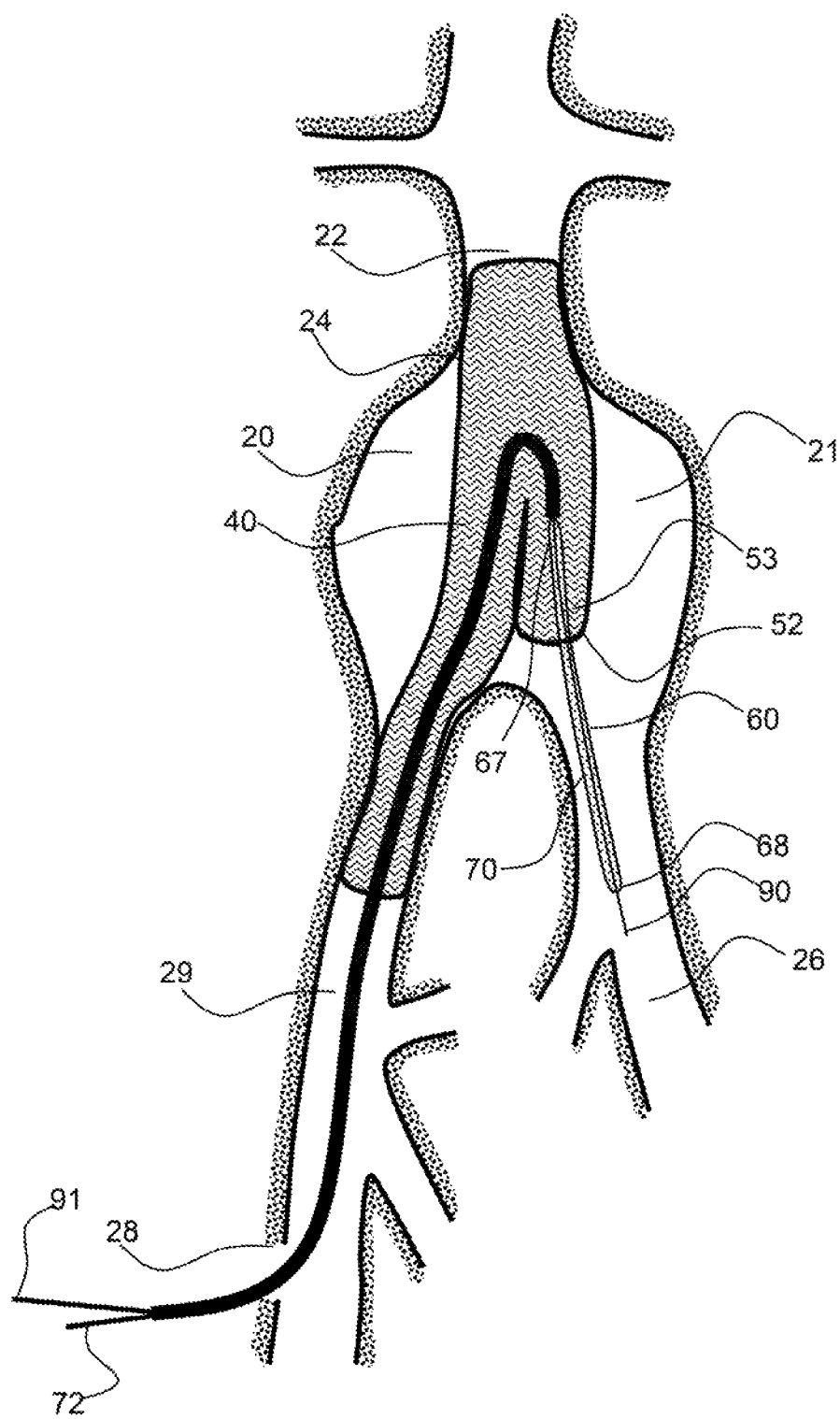
FIG. 11 shows the contralateral limb extending from the contralateral branch and into the contralateral vessel.

FIG. 11 shows the contralateral limb 60 extending from the contralateral branch 53 and into the contralateral vessel 26. The proximal end 67 of the contralateral limb 60 is configured within the contralateral branch 53 to create an overlap that secures the contralateral limb to the primary graft portion 40, when deployed.

Figure 12:
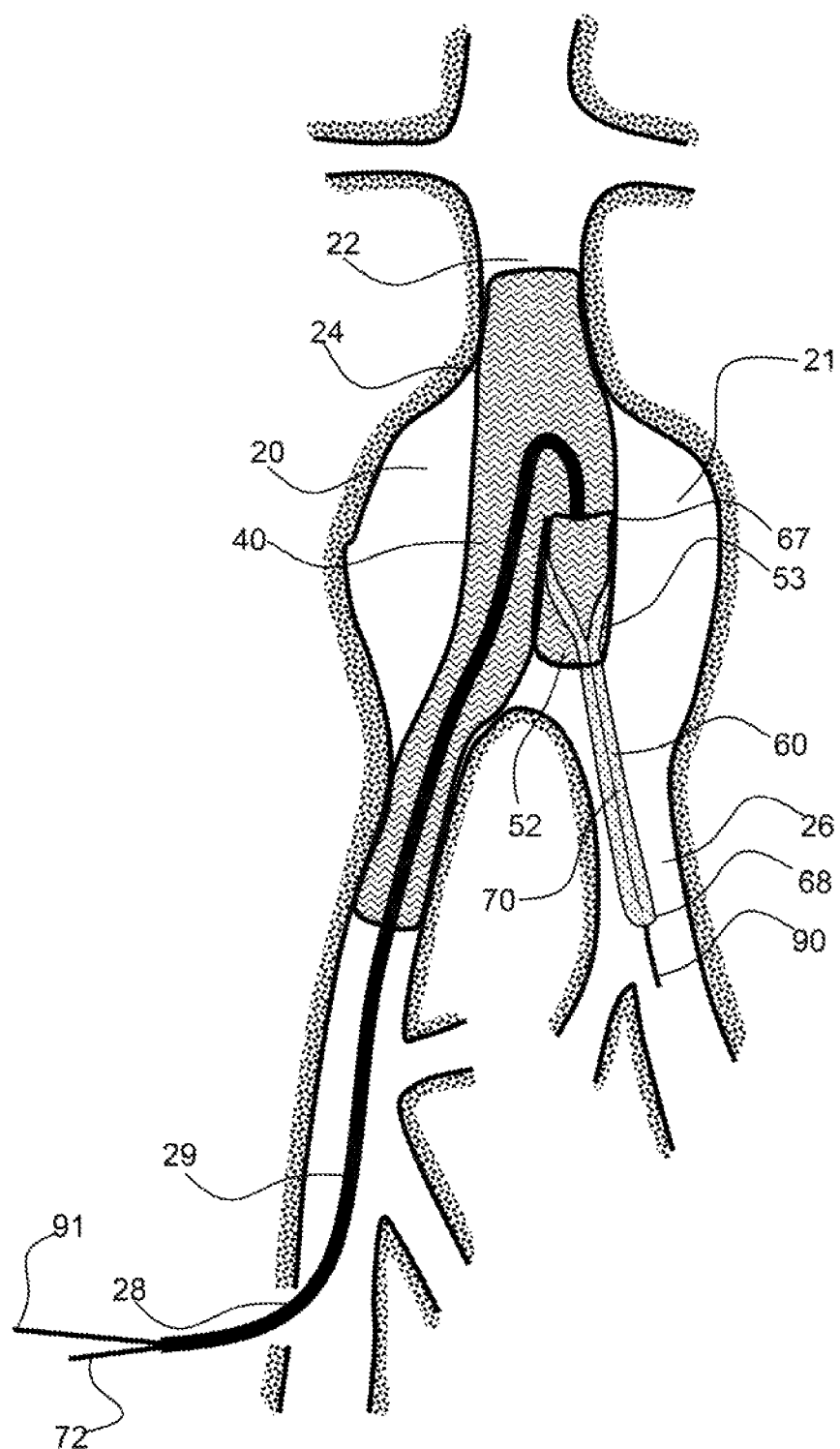
FIG. 12 shows the contralateral limb being deployed, with the proximal end expanded before the remainder of the distal end of the contralateral limb.

FIG. 12 shows the contralateral limb 60 being deployed with the proximal end 67 being expanded before the remainder of the contralateral limb. The deployment sleeve 70 is being released from the proximal end 67 first. The contralateral limb is deployed from the proximal end to the distal end or extended end 68. As shown, the extended end 68 is still restrained by the deployment sleeve 70.

Figure 13:
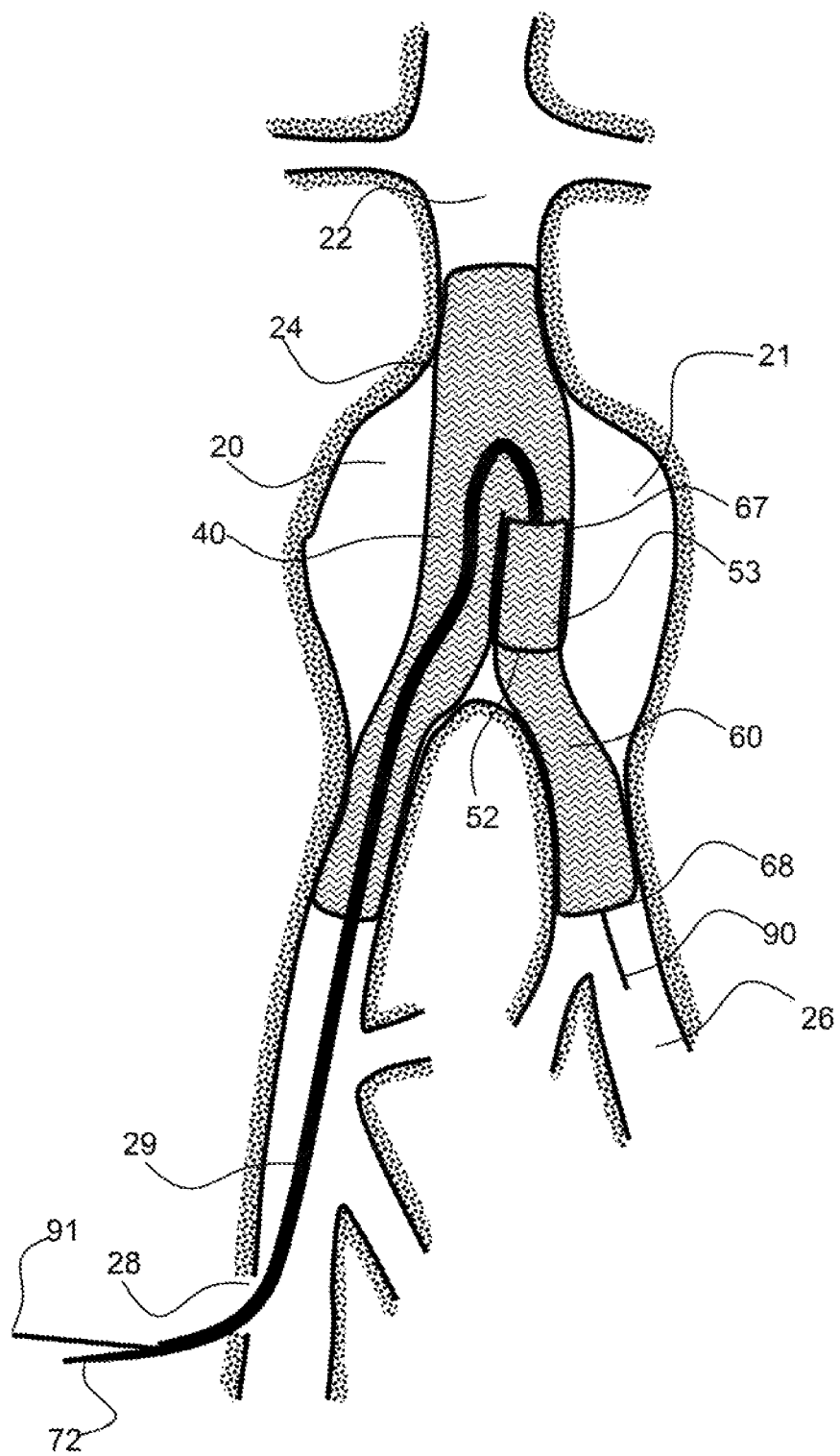
FIG. 13 shows the contralateral limb deployed and extending from the contralateral branch of the primary graft portion down into the contralateral vessel.

FIG. 13 shows the contralateral limb 60 deployed and extending from contralateral branch 53 to the contralateral vessel 26. There is an overlap of the contralateral limb 60 and the contralateral branch 53.

Figure 14:
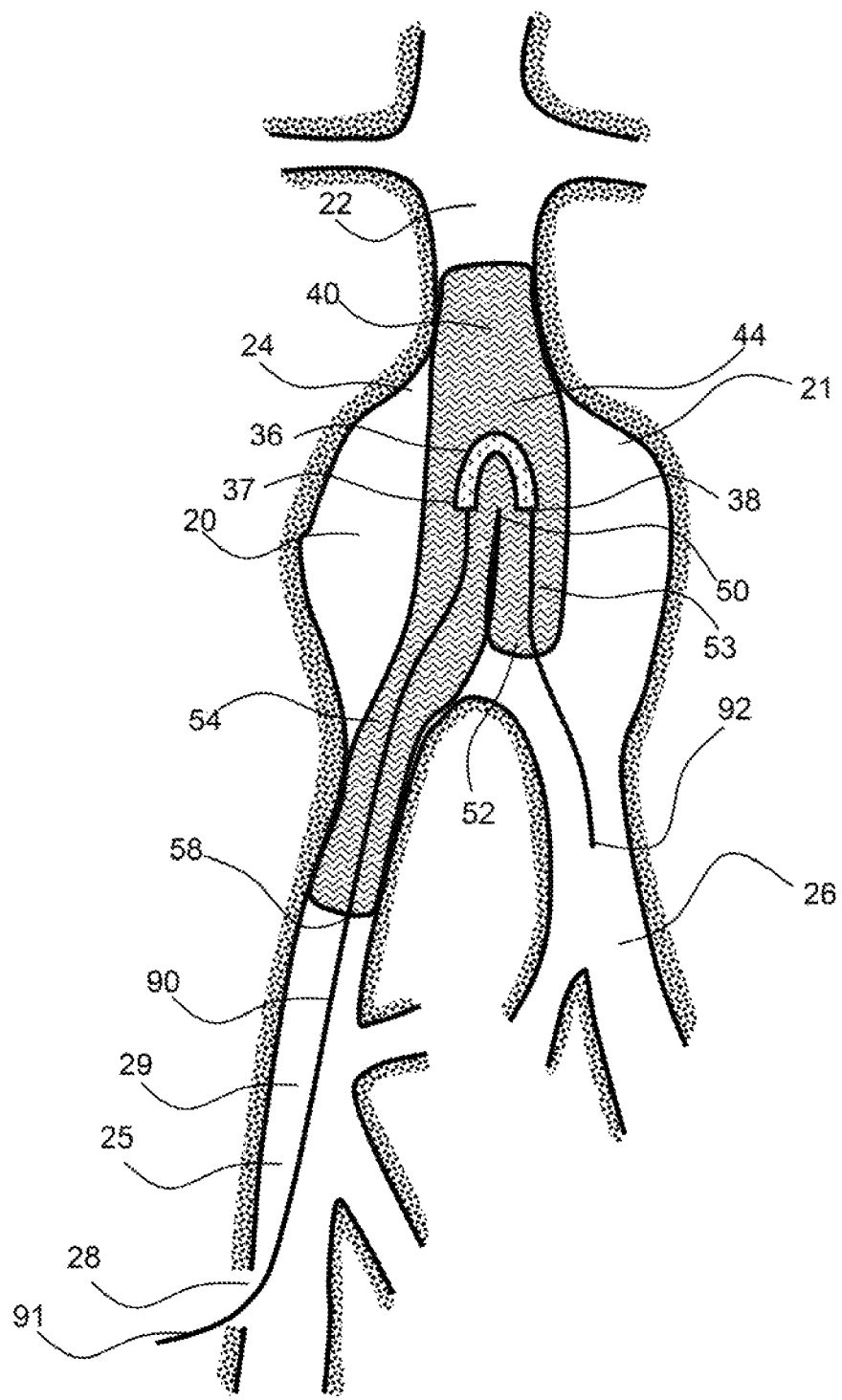
FIG. 14 shows an exemplary directional sleeve within the lumen of the primary graft portion and a guide wire being directed by said directional sleeve into the contralateral vessel of the bifurcated vascular lumen.
Figure 15:
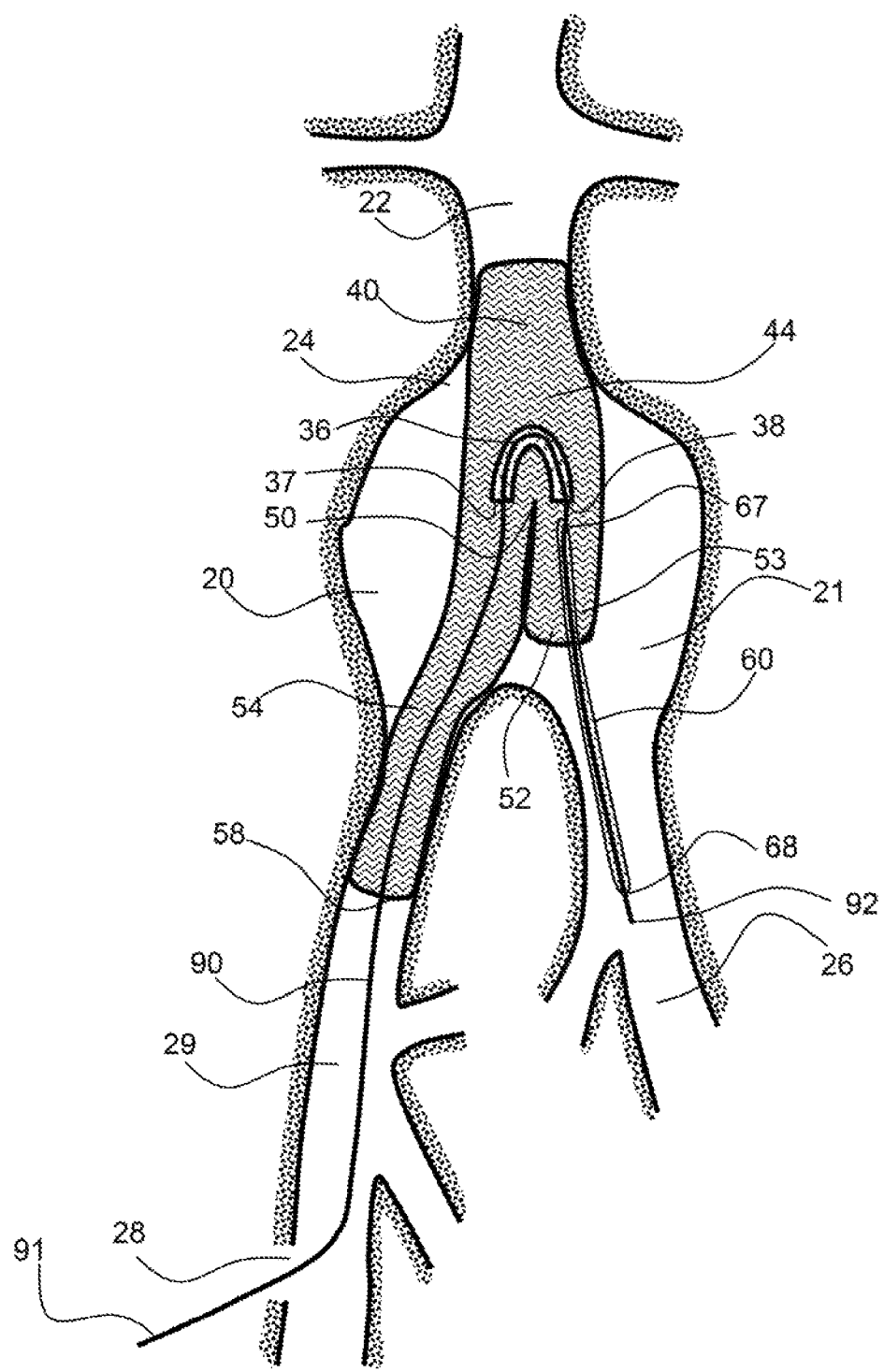
FIG. 15 shows a contralateral limb that has been traversed along the guide wire, through the directional sleeve and into the contralateral vessel.

As show in FIGS. 14 and 15, an exemplary directional sleeve 36 is configured within the lumen 44 of the primary graft portion 40 and a guide wire 90 is being directed by a directional sleeve into the contralateral vessel 26 of the bifurcated vascular lumen 20. The directional sleeve is affixed to the primary graft portion 40 and comprises a bend that guides or directs a leading end, or distal end, of a guide wire from the ipsilateral vessel 25 and into the contralateral vessel 26. A guide wire may be introduced through the access opening and then guided into the proximal opening 37 of the directional sleeve, out of the distal opening 38 of the directional sleeve before being advanced and guided into the contralateral vessel 26. FIG. 15 shows the contralateral limb configured in the contralateral vessel. A directional sleeve may be detachably attached to the primary graft portion and may be removed after the bifurcated graft is assembled in the bifurcated vessel. A tether may extend from the directional sleeve that releases the directional sleeve from the graft. The tether may extend from the graft along with a release line for deploying the stent.

Figure 16:
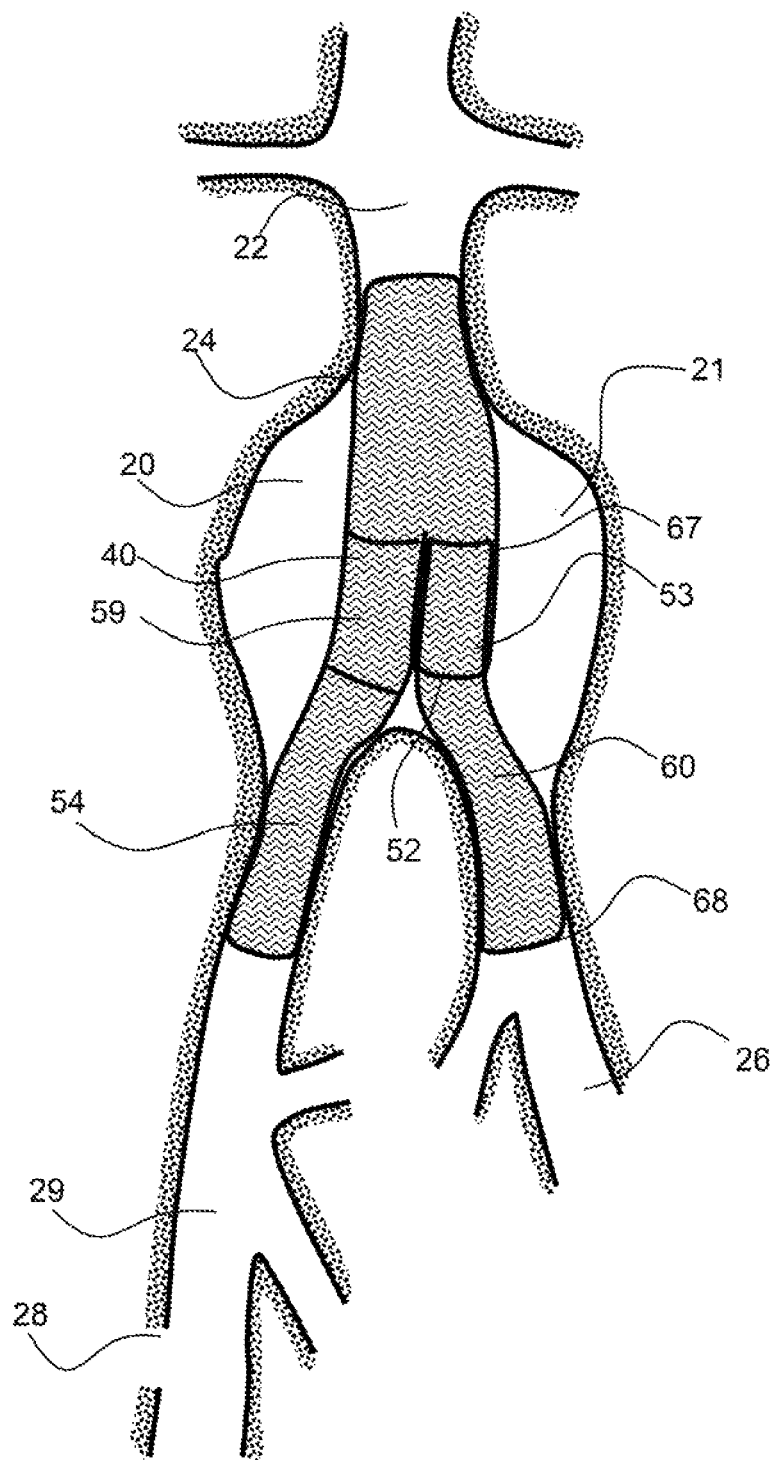
FIG. 16 shows an exemplary graft having three components, a primary graft portion, and an ipsilateral limb and a contralateral limb that are coupled to the primary graft portion.

As shown in FIG. 16, an exemplary primary graft portion 40 is configured in the bifurcated vascular lumen 20. The primary graft portion has a main body 43. The primary graft portion comprises an integral ipsilateral branch 59 having a length 62 from the graft bifurcation to the extended end 58 of the ipsilateral branch. Note that the ipsilateral branch is slightly longer than the contralateral branch 53. An ipsilateral limb 54 is coupled to the primary graft portion 40, with an overlap within the ipsilateral branch 59. A contralateral limb 60 is coupled to the primary graft portion 40, with an overlap within the contralateral branch 53. A bifurcated graft may comprise three components: a primary graft portion 40, ipsilateral limb and a contralateral limb that are coupled to the primary graft portion.

An ipsilateral extension, as used herein, is an ipsilateral branch or an ipsilateral limb, as described herein, that is an integral part of the primary graft portion.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A bifurcated vascular lumen aneurysm repair method comprising the steps of:
    a) providing a bifurcated graft comprising:
        i) a primary graft portion comprising:
            a main body having a lumen extending therethrough and a length from a distal end to a graft bifurcation:
            an integral ipsilateral extension;
            a contralateral branch;
        ii) a contralateral limb having a length from a proximal end to a distal end;
    b) accessing an ipsilateral vessel of the bifurcated vascular lumen to create an access opening into an interior conduit of the ipsilateral vessel;
    c) introducing said primary graft portion through the access opening and advancing along the interior conduit at least partially into a main vascular lumen;
        wherein the distal end of the main body is configured distal to a bifurcation in the main vascular lumen with respect to the access opening;
    d) securing said primary graft portion to the bifurcated vascular lumen;
        wherein the distal end of the main body is secured distal to an aneurysm; and
    e) passing the contralateral limb through the access opening, along the interior conduit of the ipsilateral vessel, around the bifurcation in the bifurcated vascular lumen, and at least partially into a contralateral vessel;
        wherein the distal end of the contralateral limb is configured with the contralateral vessel;
    f) securing the contralateral limb to the primary graft portion and to the contralateral vessel;
        wherein the proximal end of the contralateral limb is secured to the contralateral branch and the distal end is secured to the contralateral vessel.

2. The bifurcated vascular lumen aneurysm repair method of claim 1, wherein the proximal end of the contralateral limb is deployed before a remaining portion of the contralateral limb, whereby the contralateral limb is secured to the contralateral branch before deployment of the remaining portion of the contralateral limb.

3. The bifurcated vascular lumen aneurysm repair method of claim 1, wherein the ipsilateral extension is an ipsilateral branch and the method further comprises the step of securing an ipsilateral limb to the ipsilateral branch and to the ipsilateral vessel.

4. The bifurcated vascular lumen aneurysm repair method of claim 3, wherein the primary graft portion, the ipsilateral limb and the contralateral limb are covered stent grafts.

5. The bifurcated vascular lumen aneurysm repair method of claim 1, wherein the primary graft portion is a covered stent graft.

6. The bifurcated vascular lumen aneurysm repair method of claim 1, wherein the primary graft portion and the contralateral limb are covered stent grafts.

7. The bifurcated vascular lumen aneurysm repair method of claim 1, wherein the contralateral limb is a self-expanding covered stent graft.

8. The bifurcated vascular lumen aneurysm repair method of claim 7, wherein the self-expanding covered stent graft comprises a deployment sleeve having a release line that is configured to release the contralateral limb from a collapsed configuration within the deployment sleeve to a deployed configuration.

9. The bifurcated vascular lumen aneurysm repair method of claim 8, wherein the proximal end of the contralateral limb is deployed before a remaining portion of the contralateral limb, whereby the contralateral limb is secured to the contralateral branch before deployment of the remaining portion of the contralateral limb.

10. The bifurcated vascular lumen aneurysm repair method of claim 1, wherein the contralateral limb comprises a deployment sheath and wherein the contralateral limb is deployed by removal of the deployment sheath.

11. The bifurcated vascular lumen aneurysm repair method of claim 10, wherein the proximal end of the contralateral limb is deployed before a remaining portion of the contralateral limb, whereby the contralateral limb is secured to the contralateral branch before deployment of the remaining portion of the contralateral limb.

12. The bifurcated vascular lumen aneurysm repair method of claim 1, wherein the contralateral limb is a balloon expandable contralateral limb.

13. The bifurcated vascular lumen aneurysm repair method of claim 12, wherein the proximal end of the contralateral limb is expanded before a remaining portion of the contralateral limb, whereby the contralateral limb is expanded and secured to the contralateral branch before expansion of the remaining portion of the contralateral limb.

14. The bifurcated vascular lumen aneurysm repair method of claim 1, wherein the bifurcated vascular lumen comprises an aorta.

15. The bifurcated vascular lumen aneurysm repair method of claim 1, wherein the aneurysm is an aortic aneurysm.

16. The bifurcated vascular lumen aneurysm repair method of claim 1, wherein the step of passing the contralateral limb into the contralateral vessel comprises passing the contralateral limb over a guide wire.

17. The bifurcated vascular lumen aneurysm repair method of claim 1, further comprising the steps of:
 a) introducing a steerable sheath, having a steerable end, through the access opening and into the main body of the primary graft portion;
 b) deflecting the steerable end towards the contralateral vessel;
 c) advancing a guide wire, having a distal end, through the steerable sheath and into the contralateral vessel, wherein the distal end is within the contralateral vessel; and
 wherein the step of passing the contralateral limb into the contralateral vessel comprises:
 d) advancing the contralateral limb over the guide wire and into the contralateral vessel.

18. The bifurcated vascular lumen aneurysm repair method of claim 17, wherein the proximal end of the contralateral limb is secured before a remaining portion of the contralateral limb, whereby the contralateral limb is secured to the contralateral branch before deployment of the remaining portion of the contralateral limb.

19. The bifurcated vascular lumen aneurysm repair method of claim 1, further comprising the steps of:
 providing a sheath comprising:
  a balloon proximal to the distal end; and
  an aperture proximal to the access opening from the balloon;
 passing said sheath through the access opening and into the main body of the primary graft portion;
 expanding the balloon to secure the sheath in position with respect to the primary graft portion;
 advancing a guide wire through the sheath, out of the aperture and into a contralateral vessel of the bifurcated vascular lumen;
 wherein the step of passing the contralateral limb into the contralateral vessel comprises passing the contralateral limb over the guide wire and through the aperture in the sheath.

20. The bifurcated vascular lumen aneurysm repair method of claim 19, wherein the proximal end of the contralateral limb is secured before a remaining portion of the contralateral limb, whereby the contralateral limb is secured to the contralateral branch before deployment of the remaining portion of the contralateral limb.

21. The bifurcated vascular lumen aneurysm repair method of claim 1, wherein the primary graft portion comprises a directional sleeve configured within the lumen of the primary graft portion;
 wherein the directional sleeve has a proximal opening that faces the ipsilateral branch and a distal opening that faces toward the contralateral branch.

22. The bifurcated vascular lumen aneurysm repair method of claim 21, further comprising the steps of:
 a) advancing a guide wire through the access opening, into the proximal opening of the directional sleeve, through the directional sleeve, out of the distal opening of the directional sleeve and into the contralateral vessel;
 b) wherein the step of passing the contralateral limb into the contralateral vessel comprises passing the contralateral limb over the guide wire and through the directional sleeve.

23. The bifurcated vascular lumen aneurysm repair method of claim 22, wherein the proximal end of the contralateral limb is secured before a remaining portion of the contralateral limb, whereby the contralateral limb is secured to the contralateral branch before deployment of the remaining portion of the contralateral limb.

* * * * *